(12) United States Patent
Goldenberg et al.

(10) Patent No.: US 7,534,427 B2
(45) Date of Patent: *May 19, 2009

(54) IMMUNOTHERAPY OF B CELL MALIGNANCIES AND AUTOIMMUNE DISEASES USING UNCONJUGATED ANTIBODIES AND CONJUGATED ANTIBODIES AND ANTIBODY COMBINATIONS AND FUSION PROTEINS

(75) Inventors: David M. Goldenberg, Mendham, NJ (US); Hans J. Hansen, Picayune, MS (US)

(73) Assignee: Immunomedics, Inc., Morris Plains, NJ (US)

( * ) Notice: Subject to any disclaimer, the term of this patent is extended or adjusted under 35 U.S.C. 154(b) by 227 days.

This patent is subject to a terminal disclaimer.

(21) Appl. No.: 10/747,199

(22) Filed: Dec. 30, 2003

(65) Prior Publication Data
US 2004/0219156 A1    Nov. 4, 2004

Related U.S. Application Data

(60) Provisional application No. 60/437,145, filed on Dec. 31, 2002.

(51) Int. Cl.
- A61K 39/395 (2006.01)
- A61K 39/44 (2006.01)
- A61K 38/19 (2006.01)
- C12P 21/08 (2006.01)
- C07K 16/18 (2006.01)
- C07K 16/28 (2006.01)

(52) U.S. Cl. .................... 424/130.1; 424/9.3; 424/9.36; 424/133.1; 424/134.1; 424/135.1; 424/136.1; 424/141.1; 424/142.1; 424/144.1; 424/181.1; 424/191.1; 424/192.1; 424/193.1

(58) Field of Classification Search ........................ None
See application file for complete search history.

(56) References Cited

U.S. PATENT DOCUMENTS

| | | | |
|---|---|---|---|
| 4,036,945 A | 7/1977 | Haber | |
| 4,046,722 A | 9/1977 | Rowland | |
| 4,331,647 A | 5/1982 | Goldenberg | |
| 4,699,784 A | 10/1987 | Shih et al. | |
| 4,704,692 A | 11/1987 | Ladner et al. | |
| 4,946,778 A | 8/1990 | Ladner et al. | |
| 5,057,313 A | 10/1991 | Shih et al. | |
| 5,229,275 A | 7/1993 | Goroff et al. | |
| 5,443,953 A | 8/1995 | Hansen et al. | |
| 5,567,610 A | 10/1996 | Borrebaeck et al. | |
| 5,595,721 A | 1/1997 | Kaminski et al. | |
| 5,633,425 A | 5/1997 | Lonberg et al. | |
| 5,798,554 A | 8/1998 | Grimaldi et al. | |
| 5,827,690 A | 10/1998 | Meade et al. | |
| 5,843,439 A * | 12/1998 | Anderson et al. | 424/133.1 |
| 6,077,499 A | 6/2000 | Griffiths et al. | |
| 6,183,744 B1 * | 2/2001 | Goldenberg | 424/141.1 |
| 6,187,287 B1 | 2/2001 | Leung et al. | |
| 6,254,868 B1 | 7/2001 | Leung et al. | |
| 6,287,537 B1 * | 9/2001 | Kaminski et al. | 424/1.49 |
| 6,306,393 B1 * | 10/2001 | Goldenberg | 424/141.1 |
| 7,151,164 B2 * | 12/2006 | Hansen et al. | 530/387.3 |

FOREIGN PATENT DOCUMENTS

| WO | WO 95/09917 | * 4/1995 |
|---|---|---|
| WO | WO 00 29584 A1 | 5/2000 |
| WO | WO 00 63403 A2 | 10/2000 |

OTHER PUBLICATIONS

Ngo et al., 1994, The Protein Folding Problem and Tertiary Structure Prediction, pp. 491-495.*
Stryer et al, in Biochemistry, Third edition, W H Freeman Company, New York, pp. 31-33, 1998.*
Juweid et al, Cancer Res 55(23): 5899-5907, Dec. 1995.*
Goldenberg et al, J Clin Oncol 9(4): 548-64, Apr. 1991.*
Attwood et al, The Babel of Bioinformatics, 2000, Science vol. 290 No. 5491: 471-473.*
Skolnick et al., From genes to protein structure and function: novel applications of computational approaches in the genomic era, Jan. 2000, Trends in Biotech. 18(1): 34-39.*
Whisstock et al, Quarterly Reviews of Biophysics 36(3): 307-340, 2003.*
Griffiths et al, Clinical Cancer Res 9: 6567-6571, Dec. 2003.*
Rudikoff et al, Proc Natl Acad Sci USA 79: 1979, 1982.*
Ginaldi et al, J Clin Pathol 51: 364-369, 1998.*
Barrios et al, J Molecular Recognition 17: 332-338, 2004.*
Mack et al, Proc Natl Acad Sci USA 92: 7021-7025, 1995.*
Ansel et al., *Pharmaceutical Dosage Forms and Drug Delivery Systems*, 5th Ed., Lea & Febiger, 1990.
Baines et al., "Purification of Immunoglobulin G (IgG)", *Methods in Molecular Biology*, vol. 10, pp. 79-104, Manson (eds.), The Humana Press (1992).
Bird et al., TIBTECH, 9:132 (1991).
Carter et al., *Proc. Nat'l Acad. Sci. USA*, 89:4285 (1992).
Cochlovius et al., *Cancer Res.*, 60:4336 (2000).
Coligan et al. (eds.), *Current Protocols in Immunology*, vol. 1, pp. 2.5.1-2.6.7, 2.7.1-2.7.12, 2.8.1-2.8.10, 2.9.1-2.9.3, 2.10-2.10.4, John Wiley & Sons (1991).

(Continued)

Primary Examiner—Phuong Huynh
(74) Attorney, Agent, or Firm—Rossi, Kimms & McDowell LLP

(57) ABSTRACT

The invention is directed to a method for treating a treating and diagnosing a B cell-related disease, T cell-related disease or an autoimmune disease in a mammal by concurrently or sequentially administering to the mammal a therapeutic composition that comprises a pharmaceutically acceptable vehicle and at least one conjugated antibody, wherein predosing with a non-radiolabeled antibody is not performed.

44 Claims, No Drawings

OTHER PUBLICATIONS

Colman et al., *Biochem. Soc. Symp.*, 63:141 (1998).
Coloma et al., *Nature Biotech.*, 15:159 (1997).
Courtenay-Luck et al., "Genetic Manipulation of Antibodies", *Monoclonal Antibodies: Production, Engineering, and Clinical Application*, Ritter et al. (eds.), pp. 166-179, Cambridge University Press, 1995.
DeNardo et al., *Cancer Biother. Radiopharm.*, 13:239 (1998).
Edelman et al., *Methods in Enzymology*, vol. 1, p. 422 (Academic Press 1967).
Fitzgerald et al., *Protein Engin.*, 10(10):1221 (1997).
Freedman et al., "Non-Hodgkin's Lymphomas", *Cancer Medicine*, vol. 2, 3rd Ed., Holland et al. (eds.), pp. 2028-2068, Lea & Febiger, 1993.
Ghetie et al., *Cancer Res.*, 48:2610 (1988).
Goldenberg, *CA- A Cancer Journal for Clinicians*, 44:43 (1994).
Goldenberg et al., *Crit. Rev. Oncol/Hematol.*, 39:195 (2001).
Goldenberg et al., *J. Nucl. Med.*, 43:693 (2002).
Goodman and Gilman's "The Pharmacological Basis of Therapeutics", 7th Ed., MacMillian Publishing Co. (1985).
Govindan et al., *Current Trends Pharm. Science and Technol. Today*, 3:90 (2000).
Green et al., *Nat. Genet.*, 7:13 (1994).
Hasan et al., *Prog. Clin. Biol. Res.*, 288:471 (1989).
Hekman et al., *Cancer Immunol. Immunother.*, 32:364 (1991).
Huse et al., *Science*, 246:1274 (1989).
Johnson et al., *Curr. Opin. Struct. Biol.*, 3:5564 (1993).
Jones et al., *Nature*, 321:522 (1986).
Jori et al. (eds.), "Photodynamic Therapy of Tumors and Other Diseases", Libreria Progetto (1985).
Juweid et al., *Clin. Cancer Res.*, 5:3292s (1999).
Kaminski et al., J. Clin. Oncol., 19:3918 (2001).
Kehrl et al., B6 CD22 Workshop Panel Report, *Leukocyte Typing V, White Cell Differentiation Antigens*, Schlossman (ed.), Oxford University Press, p. 523-5, 1995.
Köhler et al., *Nature*, 256:495 (1975).
Larrick et al., *Methods: A Companion to Methods in Enzymology*, 2:106 (1991).
Leonard et al., *Blood* (suppl.), 96:578a (abstr. 2482) (2000).
Leung et al., *Hybridoma*, 13:469 (1994).
Leung et al., *J. Immunol.*, 154:5919 (1995).
Linden et al., *Clin. Cancer Res.*, 5:3287s-3291s (1999).
Linden et al., *Cancer Biother. Radiopharm*, 17:490 (2002) (abstract 47).
Lonberg et al., *Nature*, 368:856 (1994).
Longo, *Curr. Opin. Oncol.*, 8:353 (1996).
Mack et al., *Proc. Natl. Acad. Sci.*, 97:7021 (1995).
McCafferty et al., *Nature*, 348:552 (1990).
Mendez et al., *Nat. Genet.*, 15:146 (1997).
Mew et al., *J. Immunol.*, 130:1473 (1983).
Mew et al., *Cancer Res.*, 45:4380 (1985).
Nisonoff et al., *Arch. Biochem. Biophys.*, 89:230 (1960).

O'Donoghue et al., "Dosimetric Principles of Targeted Radiotherapy", *Radioimmunotherapy of Cancer*, Fritzberg (ed.), Marcel Dekker, Inc., pp. 1-20, New York, Basel (2000).
Orlandi et al., *Proc. Nat'l Acad. Sci. USA*, 86:3833 (1989).
Oseroff et al., *Proc. Nat'l Acad. Sci USA*, 83:8744 (1986).
Oseroff et al., *Photochem. Photobiol.*, 46:83 (1987).
Pastan et al., *Cell*, 47:641 (1986).
Patti et al., *Eur. J. Haematol.*, 51:18 (1993).
Pèlegrin et al., *Cancer*, 67:2529 (1991).
Porter et al., *Biochem. J.*, 73:119 (1959).
Press et al., *Cancer Res.*, 49:4906 (1989).
Press et al., *New Eng. J. Med.*, 329:1219 (1993).
Press et al., "Immunotherapy of Hodgkin's Lymphomas", *Hematol.* (*Am. Soc. Hematol. Educ. Prog.*), pp. 221-40 (2001).
Price et al., "Production and Characterization of Synthetic Peptide-Derived Antibodies", *Monoclonal Antibodies: Production, Engineering, and Clinical Application*, Ritter (eds.), pp. 60-84, Cambridge University Press, 1995.
Raag et al., *FASEB*, 9:73 (1995).
Remington's Pharmaceutical Sciences, 18th Ed., Mack Publishing Co. (1990).
Remington's Pharmaceutical Sciences, 19th Ed., Mack Publishing Co. (1995).
Reichmann et al., *Nature*, 332:323 (1988).
Ryser et al., *Proc. Natl. Acad. Sci. USA*, 75:3867 (1978).
Saltzman et al., *Biophys. J.*, 55:163 (1989).
Sandhu, *Crit. Rev. Biotech.*, 12:437 (1992).
Schlom et al., *J. Natl. Cancer Inst.*, 82:763 (1990).
Sharkey et al., *Cancer Immunol. Immunother.*, 44:179 (1997).
Sherwood et al., *Bio/Technology*, 10:1446 (1992).
Shih et al., *Int. J. Cancer*, 41:832 (1988).
Shih et al., *Int. J. Cancer*, 46:1101 (1990).
Shih et al., *Int. J. Cancer*, 56(4):538 (1994).
Singer et al., *J. Immunol.*, 150:2844 (1993).
Stein et al., *Cancer Immunol. Immunother.*, 37(5):293 (1993).
Tatsuta et al., *Lasers Surg. Med.*, 9:422 (1989).
Taylor et al., *Int. Immun.*, 6:579 (1994).
Tempest et al., *Biotechnol.*, 9:266 (1991).
Upeslacis et al., "Modification of Antibodies by Chemical Methods", *Monoclonal Antibodies: Principles and Applications*, Birch et al. (eds.), pp. 187-230, Wiley-Liss, Inc., 1995.
Verhoeyen et al., *Science*, 239:1534 (1988).
Vose et al., *J. Clin. Oncol.*, 18:1316 (2000).
Ward et al., "Genetic Manipulation and Expression of Antibodies", *Monoclonal Antibodies: Principles and Applications*, Birch et al. (eds.), pp. 137-185, Wiley-Liss, Inc. (1995).
Wiseman et al., *Crit. Rev. Oncol. Hematol.*, 39:181 (2001).
Wong et al., *Chemistry of Protein Conjugation and Cross-Linking*, CRC Press (1991).
Yu et al., *Int. J. Cancer*, 56:244 (1994).

* cited by examiner

IMMUNOTHERAPY OF B CELL MALIGNANCIES AND AUTOIMMUNE DISEASES USING UNCONJUGATED ANTIBODIES AND CONJUGATED ANTIBODIES AND ANTIBODY COMBINATIONS AND FUSION PROTEINS

CROSS-REFERENCE TO RELATED APPLICATIONS

This application is based on U.S. provisional patent application Ser. No. 60/437,145, filed Dec. 31, 2002. The entire contents of this application, including its specification, claims and drawings, are incorporated herein by reference in their entirety.

FIELD OF THE INVENTION

The present invention relates to immunotherapeutic method for treating B-cell related malignancies, particularly aggressive non-Hodgkin's lymphomas. In particular, this invention is directed to methods for treating and diagnosing a B cell-related disease, T cell-related disease or an autoimmune disease in a mammal by administering to the mammal a therapeutic composition, wherein predosing with a non-radiolabeled antibody is not performed.

BACKGROUND OF THE INVENTION

B-cell lymphomas express surface antigens that have shown to be good targets for therapy with monoclonal antibodies (Mab). Antibodies, either used alone (naked antibodies) or in conjunction with chemotherapy, can be conjugated with toxins or with radionuclides for radioimmunotherapy (RAIT). The radiolabelled antibody is administered after (Kaminski, M. S. et al., *J. Clin. Oncol.* 19:3918-3928, 2001) or together (Press, O. W. et al, New Engl. J. Med. 329:1219-24, 1993) with unlabelled antibody to improve dose distribution. Most investigators use a radiolabeled mouse antibody combined with an unlabeled antibody, which is murine or chimeric. It has been considered advantageous to radiolabel a mouse antibody from a toxicological point of view due to its shorter half-life compared to a chimeric antibody. A Mab with longer half-life gives a longer residence time of the radioimmunoconjugate in blood and bone marrow and probably thus induces more toxicity. Since the antibody in its own right hardly induces toxicity both mouse and chimeric unlabelled antibodies are used to improve dose distribution by allegedly saturating antigen on normal cells and tissues in the body (cf. Kaminski, U.S. Pat. No. 5,595,721; Wiseman et al., *Crit. Rev. Oncol. Hematol.* 39:181-194, 2001).

The use of monoclonal antibodies in targeted radiotherapy of cancers (radioimmunotherapy; RAIT) has produced striking clinical responses in hematologic diseases such as non-Hodgkin's lymphoma (NHL). New strategies are presently examined in an effort to minimize the systemic toxicity of a circulating radionuclide and the sensitization of tumors by radiation. The former being carried out by pretargeting and the latter by combination therapy with radiosenzitizing drugs. See Govindan, S. V et al., *Current Trends, Pharmaceutical Science and Technology Today* 3:90-98, 2000.

The anti-tumor activity of RAIT is mainly due to the associated radioactivity of the radiolabel attached to the antibody, which emits continuous, exponentially decreasing low-dose-rate irradiation with a heterogeneous dose deposition. Four radiolabeled antibody products are progressing towards commercialization for the RAIT of NHL. They include $^{131}$I-tositumomab (Bexxar™), $^{90}$Y-ibritumomab tiuxetan (Zevalin™), $^{90}$Y-epratuzumab (hLL2) and $^{131}$I-Lym-1. For a more detail review of these products, see Goldenberg, D. M., *Critical Reviews in Oncology/Hematology* 39:195-201, 2001, and Goldenberg, D. M., *J. Nucl. Med.* 43:693-713, 2002.

Bexxar (Corixa Corp., Seattle, Wash.) and Zevalin (IDEC-Y2B8; IDEC Pharmaceuticals, San Diego, Calif.) are both murine monoclonal antibodies (Mabs) directed against CD20 antigen expressed in the surface of normal and malignant B-lymphocytes. Bexxar is used as an IgG2a murine Mab with cold murine antibody added, whereas Zevalin has the murine antibody labeled and cold human.mouse chimeric rituximab (Rituxan™, IDEC-Genentech) added to the product. Both products provide for pretherapy cold antibody dosing in order to improve tumor targeting, which involves a 1-h infusion of 450 mg of unlabeled Bexxar antibody and a 4-6 h infusion of 450 mg of rituximab with Zevalin. Both products have shown a higher and more durable responses than naked antibodies, however, they also have dose-limiting toxicity, predominantly myelotoxicity. Zevalin was approved by the Food and Drug Administration (FDA) for the treatment of recurrent low grade or transformed B cell non-Hodgkin's lymphoma. These radiolabeled anti-CD-20 Mab must be preceded by a dose of cold antibodies to enable good tumor localization. In fact, the specific localization numbers for $^{111}$indium-Zevalin drop from 78% to 15% tumor uptake at specific tumor sites when predosing is involved (Wiseman et al., ibid).

Epratuzumab ($^{90}$Y-epratuzumab) is a humanized IgG$_1$ antibody directed against the anti-CD22 antigen. The antigen is fast internalized upon antibody binding. The naked antibody has been reported to show efficacy in follicular as well as diffuse large B-cell lymphoma (Leonard, J. P. et al., Epratuzumab (hLL2, anti-CD22 humanized monoclonal antibody) is an active and well-tolerated therapy for refractory/relapsed diffuse large B-cell non-Hodgkin's lymphoma (NHL). *Blood (Suppl)* 96:578a [abstr. 2482], 2000; Press, O. W. et al., Immunotherapy of Non-Hodgkin's Lymphomas. *Hematology (Am. Soc. Hematol. Educ. Program)*, p. 221-40, 2001). Epratuzumab is not expected to give rise to human anti-human antibodies (HAHA), which makes it suited for repeated dosing. The mouse parental antibody, mLL2, labelled with $^{131}$I and has shown efficacy in various subtypes of B-cell lymphoma (Linden, O. et al. *Clin. Cancer Res.* 5:3287s-3291 s, 1999). After internalization, the $^{131}$I-labelled antibody is dehalogenated and the radionuclide is released from the cell. Radiometals like yttrium are retained in the cell upon internalization (Sharkey, R. M., et al. *Cancer Immunol. Immunother.* 44:179-88, 1997). The shorter physical half-life of $^{90}$Y compensates in some degree for the longer half-life of epratuzumab and provides the rational for their combination.

RAIT is usually given as a single infusion. There are, however, theoretical advantages of a fractionated approach, since fractionation would better deal with the problem of heterogeneity in absorbed dose, as outlined in O'Donoghue, J. A., *Dosimetric Principles of Targeted Radiotherapy, in Radioimmunotherapy of Cancer*, A. R. Fritzberg (ed.), Marcel Dekker, Inc., p. 1-20, New York, Basel, 2000. There are also experimental data supporting that therapeutic response can be improved by splitting a large single administration of radiolabelled antibody into a number of smaller administrations (Schlom, J. et al. *J. Natl. Cancer Inst.* 82:763-71, 1990). Approaches with two infusions as well as multiple have been explored clinically using mouse antibodies (DeNardo, G. L., et al. *Cancer Biother. Radiopharm.* 13:239-54, 1998; Vose, J. M., et al. *J Clin. Oncol.* 18:1316-23, 2000).

Intratumoral variability in the expression of CD22 antigen has been reported. In fresh tumor samples from five patients, 52-89% of lymphoma cells were found to bear the antigen for the anti-CD22 MAb HD6 (Press, O. W. et al. *Cancer Res.* 49:4906-12, 1989). One alleged advantage of RAIT using long range β-emitters is their ability to kill antigen negative tumour cells in the vicinity of the targeted cells. By assessing the antigen expression of tumour cells before therapy, one could study the clinical relevance of this concept in the setting of RAIT using the anti-CD22 $^{90}$Y-labelled epratuzumab.

Research was undertaken to confirm the theoretical advantages of dose fractionation and the published experimental data that support it. The study was intended to investigate the feasibility of fractionated RAIT, using a radiolabeled humanized antibody. It was found that after predosing with 100 mg of the humanized CD22 Mab, epratuzumab, labelled with $^{111}$In for dosimetry purposes, subsequent fractionated doses of $^{90}$Y-labelled epratuzumab at doses of up to 7.5 mCi/m$^2$, once weekly for up to 2-3 weeks, resulted in tolerable and effective radioimmunotherapy (Linden et al., *Cancer Biother Radiopharm* 2002; 17: 490 [abstract 47]. Although these clinical studies suggest that fractionated therapy of a radioimmunoconjugate is feasible, no comparison was made with administered a single high-dose of the radioimmunoconjugate in terms of safety and efficacy. Since the first "dosimetry" dose with $^{111}$In contained 100 mg of antibody, and each susccessive injection also contained this naked antibody dose, it also could not be determined if these doses that totalled at least 300 mg of epratuzumab also served as a predosing effect as suggested in other cited studies involving CD20 antibodies. Therefore, it was not interpretable from these studies whether or not any predosing was needed for such radioimmunotherapy, particularly with CD22 antibodies.

We have now found that predosing is not used in this invention, contrary to other published studies and Kaminski's U.S. Pat. No. 5,595,721, to saturate the antigenic sites in the normal tissues and spleen, as practiced in the prior art. Clearly, the invention disclosed herein shows that there is a lack of a need of high antibody predosing, as practiced in the prior art.

SUMMARY OF THE INVENTION

Accordingly, it is an object of the present invention to provide methods for treating a disease in a mammal by administering a therapeutic composition wherein predosing with a non-radiolabeled antibody, fragment or fusion protein is not performed.

It is also an object of the current invention to make the above-mentioned methods not only simple and easy for administration, yet by themselves, remain therapeutically active and have similar response rates without having a higher dose of naked antibody affecting the tumor.

It is further an object of the invention to provide methods that show a more effective response in treating aggressive non-Hodgkin's lymphoma, in contrast to what is demonstrated by the prior art that only shows effects in indolent forms of lymphoma.

These and other objects are achieved, in accordance with an embodiment of the present invention, by provision of a method for treating a disease in a mammal comprising concurrently or sequentially administering to the mammal a therapeutic composition that comprises a pharmaceutically acceptable vehicle and at least one conjugated antibody or a fragment thereof or a conjugated antibody fusion protein or a fragment thereof, wherein predosing with a non-radiolabeled antibody, fragment or fusion protein is not performed. The unconjugated antibody, fragment or fusion protein is optionally added with the conjugated antibody, fragment or fusion protein, as a maintenance therapy to keep tumor cells from target escape.

In a preferred embodiment, the present invention is directed to a method for treating diseases such as B-cell-related malignancies. In addition, it is also useful for treating autoimmune diseases, as well as T-cell-related malignancies.

In another preferred embodiment, the conjugated and unconjugated antibodies, fragments, and fusion proteins of the present invention can be targeted against an antigen selected from the group consisting of CD3, CD4, CD5, CD8, CD11c, CD14, CD15, CD19, CD20, CD21, CD22, CD23, CD25, CD33, CD37, CD38, CD40, CD40L, CD52, CD54, CD74, CD80, CD126, Ia, HMI.24, HLA-DR, tenascin, MUC1 and B-cell-tumor-associated antigens, including vascular endothelial antigens, such as vascular endothelial growth factor (VEGF) and placenta growth factor (PlGF). In a related vein, the conjugated and/or unconjugated antibodies, fragments or fusion proteins of the present invention can be the same or different. In addition, these antibodies can be human, murine, chimeric, subhuman primatized or humanized. Furthermore, these antibodies, fragments or fusion proteins can be selected from the group consisting of intact IgG, F(ab')$_2$, F(ab)$_2$, Fab', Fab, scFvs, diabodies, triabodies or tetrabodies and can be conjugated to at least one therapeutic agent.

In accordance with another aspect of the present invention, a method is provided as described above, wherein mammalian subjects, such as humans and domestic or companion animals, are treated with one or more antibodies that are conjugated to one or more therapeutic agents selected from the group consisting of drug, toxin, immunomodulator, chelator, boron compounds, photodynamic agent, and radionuclide.

In yet another preferred embodiment, the therapeutic composition comprises a fusion protein of said combination of antibodies or antibodies with immunomodulators. The fused antibodies can comprise antibodies against different antigens as well as antibodies against different epitopes of the same antigen.

The present invention contemplates the above-mentioned method wherein the conjugated and unconjugated antibody is an anti-CD22 monoclonal that is parenterally administered into a mammal at a preferable dosage of 20-600 milligrams protein per dose, more preferably at 20-150 milligrams protein per dose, and most preferably, at 20-100 milligrams protein per dose. In addition, the mammal may receive the anti-CD22 antibody as repeated parenteral dosages of preferably 20-150 milligrams protein per dose and more preferably, 20-100 mg protein per dose. It is important to recognize that such doses are given as the actual therapeutic dose without requiring any predosing, either for improving targeting or for dosimetric purposes, as practiced previously by, for example, Juweid et al., *Clin. Cancer Res.* 5:3292s-3303s, 1999 (where a prior dose of 50 mg of the CD22 Mab conjugated with $^{111}$In or another diagnostic isotope was required). No attempt was made in such studies to assess the ability of the therapeutic radioimmunoconjugate with various protein doses of the antibody to be effective directly without a prior dosing regimen.

In another preferred embodiment, the method for treating a disease in a mammal comprises administering to the mammal a therapeutic composition comprising a pharmaceutically acceptable vehicle and a multispecific multivalent antibody, fragment or fusion protein conjugate that binds to at least one target antigen and a therapeutic agent, wherein predosing with a non-radiolabeled antibody is not performed.

In yet another preferred embodiment, the method for treating a disease in mammals comprises:

(a) administering to the mammal a composition that comprises a multispecific multivalent antibody, fragment or fusion protein that binds to at least one target antigen;

(b) optionally, a clearing agent to allow the composition to clear non-localized antibodies from circulation; and (c) administering to the mammal a pharmaceutially effective amount of therapeutic conjugate that binds to the multispecific multivalent antibody, fragment or fusion protein, and wherein predosing with a non-radiolabeled antibody is not performed.

Other objects, features and advantages of the present invention will become apparent from the following detailed description and appended claims.

DETAILED DESCRIPTION OF THE PREFERRED EMBODIMENTS

Unless otherwise specified, "a" or "an" means "one or more".

1. Definitions

In the description that follows, a number of terms are used and the following definitions are provided to facilitate understanding of the present invention.

Non-Hodgkin's lymphoma (NHL) refers to a family of lymphoma diseases that involves lymph nodes, spleen, other organs and often the bone marrow There are at least 30 different types of NHL. The two common types are follicular (low grade or indolent) and aggressive, diffuse large cell (intermediate or high grade) lymphomas.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as $F(ab')_2$, $F(ab)_2$, Fab', Fab, Fv, sFv and the like. Regardless of structure, an antibody fragment binds with the same antigen that is recognized by the intact antibody. For example, an anti-CD22 monoclonal antibody fragment binds with an epitope of CD22. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A naked or cold antibody is generally an entire antibody which is not conjugated (unconjugated) to a therapeutic agent. This is so because the Fc portion of the antibody molecule provides effector functions, such as complement fixation and ADCC (antibody dependent cell cytotoxicity), which set mechanisms into action that may result in cell lysis. However, it is possible that the Fc portion is not required for therapeutic function, with other mechanisms, such as apoptosis, coming into play. Naked antibodies are also non-radiolabeled antibodies that include both polyclonal and monoclonal antibodies, as well as certain recombinant antibodies, such as primatized subhuman, chimeric, humanized or human antibodies.

A chimeric antibody is a recombinant protein that contains the variable domains including the complementarity determining regions (CDRs) of an antibody derived from one species, preferably a rodent antibody, while the constant domains of the antibody molecule is derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, is transferred from the heavy and light variable chains of the rodent antibody into human heavy and light variable domains. The constant domains of the antibody molecule is derived from those of a human antibody.

A human antibody is an antibody obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564-571 (1993).

Human antibodies may also be generated by in vitro activated B cells. See U.S. Pat. Nos. 5,567,610 and 5,229,275, which are incorporated in their entirety by reference.

A therapeutic agent is a molecule or atom which is administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, drugs, toxins, nucleases, hormones, immunomodulators, chelators, boron compounds, photoactive agents or dyes and radioisotopes.

An immunomodulator is a therapeutic agent as defined in the present invention that when present, alters, suppresses or stimulates the body's immune system. Typically, the immunomodulator useful in the present invention stimulates immune cells to proliferate or become activated in an immune response cascade, such as macrophages, B-cells, and/or T-cells.

An immunoconjugate is a conjugate of an antibody component with a therapeutic or diagnostic agent. The diagnostic agent can comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope.

An expression vector is a DNA molecules comprising a gene that is expressed in a host cell. Typically, gene expression is placed under the control of certain regulatory elements, including constitutive or inducible promoters, tissue-specific regulatory elements and enhancers. Such a gene is said to be "operably linked to" the regulatory elements.

A recombinant host may be any prokaryotic or eukaryotic cell that contains either a cloning vector or expression vector. This term also includes those prokaryotic or eukaryotic cells, as well as an transgenic animal, that have been genetically engineered to contain the cloned gene(s) in the chromosome or genome of the host cell or cells of the host cells. Suitable mammalian host cells include myeloma cells, such as SP2/0 cells, and NS0 cells, as well as Chinese Hamster Ovary (CHO) cells, hybridoma cell lines and other mammalian host cell useful for expressing antibodies. Also particularly useful to express mAbs and other fusion proteins, is a human cell line, PER.C6 disclosed in WO 0063403 A2, which produces 2 to 200-fold more recombinant protein as compared to conventional mammalian cell lines, such as CHO, COS, Vero, Hela, BHK and SP2-cell lines. Special transgenic animals with a modified immune system are particularly useful for making fully human antibodies.

As used herein, the term antibody fusion protein is a recombinantly produced antigen-binding molecule in which two or more of the same or different single-chain antibody or antibody fragment segments with the same or different specificities are linked. Valency of the fusion protein indicates how many binding arms or sites the fusion protein has to a single antigen or epitope; i.e., monovalent, bivalent, trivalent or mutlivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only binds with one epitope, for example a diabody with two binding site reactive with the same antigen. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

A multispecific antibody is an antibody that can bind simultaneously to at least two targets that are of different structure, e.g., two different antigens, two different epitopes on the same antigen, or a hapten and/or an antigen or epitope. One specificity would be for a B-cell, T-cell, myeloid-, plasma-, and mast-cell antigen or epitope. Another specificity could be to a different antigen on the same cell type, such as CD3, CD4, CD5, CD8, CD11c, CD 14, CD15, CD19, CD20, CD21, CD22, CD23, CD25, CD33, CD37, CD38, CD40, CD40L, CD52, CD54, CD74, CD80, CD126, Ia, HMI.24, HLA-DR, tenascin, MUC1 and a B-cell-tumor-associated antigen, including vascular endothelial antigens, such as VEGF and PIGF. Multispecific, multivalent antibodies are constructs that have more than one binding site, and the binding sites are of different specificity. For example, a diabody, where one binding site reacts with one antigen and the other with the another antigen.

A bispecific antibody is an antibody that can bind simultaneously to two targets which are of different structure. Bispecific antibodies (bsAb) and bispecific antibody fragments (bsFab) have at least one arm that specifically binds to, for example, a B-cell, T-cell, myeloid-, plasma-, and mast-cell antigen or epitope and at least one other arm that specifically binds to a targetable conjugate that bears a therapeutic or diagnostic agent. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with a binding site for one antigen and two scFv with two binding sites for a second antigen.

Caninized or felinized antibodies are recombinant proteins in which rodent (or another species) complementarity-determining regions of a monoclonal antibody have been transferred from heavy and light variable chains of rodent (or another species) immunoglobulin into a dog or cat, respectively, immunoglobulin variable domain.

Subhuman primatized antibodies are recombinant proteins in which subhuman primate (e.g., monkey) complementarity-determining regions of a monoclonal antibody have been transferred from heavy and light varian chains of roden (or another species) immunoglobulin into a subhuman primate immunoglobulin variable domain.

Domestic animals include large animals such as horses, cattle, sheep, goats, llamas, alpacas, and pigs, as well as companion animals. In a preferred embodiment, the domestic animal is a horse.

Companion animals include animals kept as pets. These are primarily dogs and cats, although small rodents, such as guinea pigs, hamsters, rats, and ferrets, are also included, as are subhuman primates such as monkeys. In a preferred embodiment the companion animal is a dog or a cat.

The term "clearing agent" refers to an antibody which binds the binding site of the targeting moiety, wherein the targeting moiety can be an antibody, an antigen-binding antibody fragment or a non-antibody targeting moiety. In a more preferred method, the clearing agent is a monoclonal antibody that is an anti-idiotypic to the monoclonal antibody of the conjugate used in the first step, as described in U.S. application Ser. No. 08/486,166. In another preferred embodiment, the clearing agent is substituted with multiple residues of carbohydrate, such as galactose, which allow the clearing agent to be cleared quickly from circulation by asialoglycoprotein receptors in the liver.

2. Preparation of Monoclonal Antibodies including Chimeric, Humanized and Human Antibodies Monoclonal antibodies (MAbs) are a homogeneous population of antibodies to a particular antigen and the antibody comprises only one type of antigen binding site and binds to only one epitope on an antigenic determinant.

Rodent monoclonal antibodies to specific antigens may be obtained by methods known to those skilled in the art. See, for example, Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions.

General techniques for cloning murine immunoglobulin variable domains are described, for example, by the publication of Orlandi et al., *Proc. Natl. Acad. Sci. USA* 86:3833 (1989), which is incorporated by reference in its entirety. Techniques for constructing chimeric antibodies are well known to those of skill in the art. As an example, Leung et al., *Hybridoma* 13:469 (1994), describe how they produced an LL2 chimera by combining DNA sequences encoding the $V_\kappa$ and $V_H$ domains of LL2 monoclonal antibody, an anti-CD22 antibody, with respective human κ and $IgG_1$ constant region domains. This publication also provides the nucleotide sequences of the LL2 light and heavy chain variable regions, $V_\kappa$ and $V_H$, respectively. Techniques for producing humanized MAbs are described, for example, by Jones et al., *Nature* 321: 522 (1986), Riechmann et al., *Nature* 332: 323 (1988), Verhoeyen et al., *Science* 239: 1534 (1988), Carter et al., *Proc. Natl. Acad. Sci. USA* 89: 4285 (1992), Sandhu, *Crit. Rev. Biotech.* 12: 437 (1992), and Singer et al., *J. Immun.* 150:2844 (1993), each of which is hereby incorporated by reference.

A chimeric antibody is a recombinant protein that contains the variable domains including the CDRs derived from one species of animal, such as a rodent antibody, while the remainder of the antibody molecule; i.e., the constant domains, is derived from a human antibody. Accordingly, a chimeric monoclonal antibody can also be humanized by replacing the sequences of the murine FR in the variable domains of the chimeric mAb with one or more different human FR. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more some human residues in the FR regions with their murine counterparts to obtain an anatibody that possesses good binding affinity to its epitope. See, for example, Tempest et al., *Biotechnology* 9:266 (1991) and Verhoeyen et al., *Science* 239: 1534 (1988). Further, the affinity of humanized, chimeric and human MAbs to a specific epitope can be increased by mutagenesis of the CDRs, so that a lower dose of antibody may be as effective as a higher dose of a lower affinity MAb prior to mutagenesis. See for example, WO0029584A1.

Another method for producing the antibodies of the present invention is by production in the milk of transgenic livestock. See, e.g., Colman, A., *Biochem. Soc. Symp.*, 63:141-147, 1998; U.S. Pat. No. 5,827,690, both of which are incoporated in their entirety by reference. Two DNA constructs are prepared which contain, respectively, DNA segments encoding paired immunoglobulin heavy and light chains. The DNA segments are cloned into expression vectors which contain a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

A fully human antibody of the present invention, i.e., human anti-CD20 MAbs or other human antibodies, such as anti-CD19, anti-CD22, anti-CD21 or anti-CD23 MAbs for combination therapy with humanized, chimeric or human anti-CD20 antibodies, can be obtained from a transgenic non-human animal. See, e.g., Mendez et al., *Nature Genetics* 15:146-156 (1997); U.S. Pat. No. 5,633,425, both of which are incorporated in their entirety by reference. For example, a human antibody can be recovered from a transgenic mouse possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Further recent methods for producing bispecific mAbs include engineered recombinant mAbs which have additional cysteine residues so that they crosslink more strongly than the more common immunoglobulin isotypes. See, e.g., FitzGerald et al., Protein Eng. 10(10):1221-1225, 1997. Another approach is to engineer recombinant fusion proteins linking two or more different single-chain antibody or antibody fragment segments with the needed dual specificities. See, e.g., Coloma et al., Nature Biotech. 15:159-163, 1997. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with two binding sites for one antigen and two scFv with two binding sites for a second antigen.

Bispecific fusion proteins linking two or more different single-chain antibodies or antibody fragments are produced in similar manner. Recombinant methods can be used to produce a variety of fusion proteins. For example a fusion protein comprising a Fab fragment derived from a humanized monoclonal anti-CD20 antibody and a scFv derived from a murine anti-diDTPA can be produced. A flexible linker, such as GGGS connects the scFv to the constant region of the heavy chain of the anti-CD20 antibody. Alternatively, the scFv can be connected to the constant region of the light chain of another humanized antibody. Appropriate linker sequences necessary for the in-frame connection of the heavy chain Fd to the scFv are introduced into the VL and VK domains through PCR reactions. The DNA fragment encoding the scFv is then ligated into a staging vector containing a DNA sequence encoding the CH1 domain. The resulting scFv-CH1 construct is excised and ligated into a vector containing a DNA sequence encoding the VH region of an anti-CD20 antibody. The resulting vector can be used to transfect an appropriate host cell, such as a mammalian cell for the expression of the bispecific fusion protein.

Examples of such bivalent and bispecific antibodies are found in U.S. patent application 60/399,707, filed Aug. 1, 2002; 60/360,229, filed Mar. 1, 2002; 60/388,314, filed Jun. 14, 2002; and Ser. No. 10/116,116, filed Apr. 5, 2002, all of which are incorporated by reference herein.

3. Production of Antibody Fragments

Antibody fragments which recognize specific epitopes can be generated by known techniques. The antibody fragments are antigen binding portions of an antibody, such as F(ab')$_2$, Fab', Fab, Fv, sFv and the like. Other antibody fragments include, but are not limited to: the F(ab)'$_2$ fragments which can be produced by pepsin digestion of the antibody molecule and the Fab' fragments, which can be generated by reducing disulfide bridges of the F(ab)'2 fragments. Alternatively, Fab' expression expression libraries can be constructed (Huse et al., 1989, Science 246:1274-1281) to allow rapid and easy identification of monoclonal Fab' fragments with the desired specificity. The present invention encompasses antibodies and antibody fragments.

A single chain Fv molecule (scFv) comprises a VL domain and a VH domain. The VL and VH domains associate to form a target binding site. These two domains are further covalently linked by a peptide linker (L). A scFv molecule is denoted as either VL-L-VH if the VL domain is the N-terminal part of the scFv molecule, or as VH-L-VL if the VH domain is the N-terminal part of the scFv molecule. Methods for making scFv molecules and designing suitable peptide linkers are described in U.S. Pat. No. 4,704,692, U.S. Pat. No. 4,946,778, R. Raag and M. Whitlow, "*Single Chain Fvs.*" FASEB 9:73-80 (1995) and R. E. Bird and B. W. Walker, *Single Chain Antibody Variable Regions*, TIBTECH 9:132-137 (1991). These references are incorporated herein by reference.

An antibody fragment can be prepared by proteolytic hydrolysis of the full length antibody or by expression in *E. coli* or another host of the DNA coding for the fragment. An antibody fragment can be obtained by pepsin or papain digestion of full length antibodies by conventional methods. For example, an antibody fragment can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using papain produces two monovalent Fab fragments and an Fc fragment directly. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89:230 (1960); Porter, *Biochem. J.* 73:119 (1959), Edelman et al., in METHODS IN ENZYMOLOGY, Volume 1, p. 422 (Academic Press 1967), and Coligan at pages 2.8.1-2.8.10 and 2.10.-2.10.4.

Another form of an antibody fragment is a peptide coding for a single complementarity-determining region (CDR). A CDR is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2:106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

4. Multispecific and Multivalent Antibodies

The antibodies having the same specificities, as well as other those having different specificities for use in combination therapy, described herein, can also be made as multispecific antibodies (comprising at least one binding site to a CD20 epitope or antigen and at least one binding site to another epitope on CD20 or another antigen) and multivalent antibodies (comprising mutliple binding sites to the same epitope or antigen).

The present invention provides a bispecific antibody or antibody fragment having at least a binding region that specifically binds a targeted cell marker and at least one other binding region that specifically binds a targetable conjugate. The targetable conjugate comprises a carrier portion which comprises or bears at least one epitope recognized by at least one binding region of the bispecific antibody or antibody fragment.

A variety of recombinant methods can be used to produce bispecific antibodies and antibody fragments as described above.

An multivalent antibody is also contemplated in the present invention. This multivalent target binding protein is constructed by association of a first and a second polypeptide. The first polypeptide comprises a first single chain Fv molecule covalently linked to a first immunoglobulin-like domain which preferably is an immunoglobulin light chain variable region domain. The second polypeptide comprises a second single chain Fv molecule covalently linked to a second immunoglobulin-like domain which preferably is an immunoglobulin heavy chain variable region domain. Each of the first and second single chain Fv molecules forms a target binding site, and the first and second immunoglobulin-like domains associate to form a third target binding site.

A single chain Fv molecule with the VL-L-VH configuration, wherein L is a linker, may associate with another single chain Fv molecule with the VH-L-VL configuration to form a bivalent dimer. In this case, the VL domain of the first scFv and the VH domain of the second scFv molecule associate to form one target binding site, while the VH domain of the first scFv and the VL domain of the second scFv associate to form the other target binding site.

Another embodiment of the present invention is bispecific, trivalent targeting protein comprising two heterologous polypeptide chains associated non-covalently to form three binding sites, two of which have affinity for one target and a third which has affinity for a hapten that can be made and attached to a carrier for a diagnostic and/or therapeutic agent. Preferably, the binding protein has two similar antigenic binding sites and a different antigenic binding site. The bispecific, trivalent targeting agents have two different scFvs, one scFv contains two $V_H$ domains from one antibody connected by a short linker to the $V_L$ domain of another antibody and the second scFv contains two $V_L$ domains from the first antibody connected by a short linker to the $V_H$ domain of the other antibody. The methods for generating multivalent, multispecific agents from $V_H$ and $V_L$ domains provide that individual chains synthesized from a DNA plasmid in a host organism are composed entirely of $V_H$ domains (the $V_H$-chain) or entirely of $V_L$ domains (the $V_L$-chain) in such a way that any agent of multivalency and multispecificity can be produced by non-covalent association of one $V_H$-chain with one $V_L$-chain. For example, forming a trivalent, trispecific agent, the $V_H$-chain will consist of the amino acid sequences of three $V_H$ domains, each from an antibody of different specificity, joined by peptide linkers of variable lengths, and the $V_L$-chain will consist of complementary $V_L$ domains, joined by peptide linkers similar to those used for the $V_H$-chain. Since the $V_H$ and $V_L$ domains of antibodies associate in an anti-parallel fashion, the preferred method in this invention has the $V_L$ domains in the $V_L$-chain arranged in the reverse order of the $V_H$ domains in the $V_H$-chain.

5. Diabodies, Triabodies and Tetrabodies

The antibodies of the present invention can also be used to prepare functional bispecific single-chain antibodies (bs-cAb), also called diabodies, and can be produced in mammalian cells using recombinant methods. See, e.g., Mack et al., Proc. Natl. Acad. Sci., 92:7021-7025, 1995, incorporated. For example, bscAb are produced by joining two single-chain Fv fragments via a glycine-serine linker using recombinant methods. The V light-chain ($V_L$) and V heavy-chain ($V_H$) domains of two antibodies of interest are isolated using standard PCR methods. The $V_L$ and $V_H$ cDNA's obtained from each hybridoma are then joined to form a single-chain fragment in a two-step fusion PCR. The first PCR step introduces the $(Gly_4\text{-}Ser_1)_3$ linker, and the second step joins the $V_L$ and $V_H$ amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into an eukaryotic expression vector. Functional protein expression can be obtained by transfecting the vector into chinese hamster ovary cells. Bispecific fusion proteins are prepared in a similar manner. Bispecific single-chain antibodies and bispecific fusion proteins are included within the scope of the present invention.

For example, a humanized, chimeric or human anti-CD22 monoclonal antibody can be used to produce antigen specific diabodies, triabodies, and tetrabodies. The monospecific diabodies, triabodies, and tetrabodies bind selectively to targeted antigens and as the number of binding sites on the molecule increases, the affinity for the target cell increases and a longer residence time is observed at the desired location. For diabodies, the two chains comprising the $V_H$ polypeptide of the humanized CD22 MAb connected to the $V_\kappa$ polypeptide of the humanized CD22 MAb by a five amino acid residue linker are utilized. Each chain forms one half of the humanized CD22 diabody. In the case of triabodies, the three chains comprising $V_H$ polypeptide of the humanized CD22 MAb connected to the $V_\kappa$ polypeptide of the humanized CD22 MAb by no linker are utilized. Each chain forms one third of the hCD22 triabody.

The preferred use of the bispecific diabodies described herein is for pre-targeting CD22 positive tumors for subsequent specific delivery of diagnostic or therapeutic agents. These diabodies bind selectively to targeted antigens allowing for increased affinity and a longer residence time at the desired location. Moreover, non-antigen bound diabodies are cleared from the body quickly and exposure of normal tissues is minimized. The diagnostic and therapeutic agents can include isotopes, drugs, toxins, cytokines, hormones, growth factors, conjugates, radionuclides, and metals. For example, gadolinium metal is used for magnetic resonance imaging (MRI). Examples of radionuclides are $^{225}$Ac, $^{18}$F, $^{68}$Ga, $^{67}$Ga, $^{90}$Y, $^{86}$Y, $^{111}$In, $^{131}$I, $^{125}$I, $^{123}$I, $^{99m}$Tc, $^{94m}$Tc, $^{186}$Re, $^{188}$Re, $^{177}$Lu, $^{62}$Cu, $^{64}$Cu, $^{67}$Cu, $^{212}$Bi, $^{213}$Bi, $^{32}$P, $^{11}$C, $^{13}$N, $^{15}$O, $^{76}$Br, and $^{211}$At. Other radionuclides are also available as diagnostic and therapeutic agents, especially those in the energy range of 60 to 4,000 keV.

More recently, a tetravalent tandem diabody (termed tandab) with dual specificity has also been reported (Cochlovius et al., Cancer Research (2000) 60:4336-4341). The bispecific tandab is a dimer of two identical polypeptides, each containing four variable domains of two different antibodies ($V_{H1}$, $V_{L1}$, $V_{H2}$, $V_{L2}$) linked in an orientation to facilitate the formation of two potential binding sites for each of the two different specificities upon self-association.

6. Conjugated Multivalent and Multispecific Antibodies

In another embodiment of the instant invention is a conjugated multivalent antibody. Additional amino acid residues may be added to either the N- or C-terminus of the first or the second polypeptide. The additional amino acid residues may comprise a peptide tag, a signal peptide, a cytokine, an enzyme (for example, a pro-drug activating enzyme), a hormone, a peptide toxin, such as pseudomonas extoxin, a peptide drug, a cytotoxic protein or other functional proteins. As used herein, a functional protein is a protein which has a biological function.

In one embodiment, drugs, toxins, radioactive compounds, enzymes, hormones, cytotoxic proteins, chelates, cytokines and other functional agents may be conjugated to the multivalent target binding protein, preferably through covalent attachments to the side chains of the amino acid residues of the multivalent target binding protein, for example amine, carboxyl, phenyl, thiol or hydroxyl groups. Various conventional linkers may be used for this purpose, for example, diisocyanates, diisothiocyanates, bis(hydroxysuccinimide) esters, carbodiimides, maleimide-hydroxysuccinimide esters, glutaraldehyde and the like. Conjugation of agents to the multivalent protein preferably does not significantly affect the protein's binding specificity or affinity to its target. As used herein, a functional agent is an agent which has a biological function. A preferred functional agent is a cytotoxic agent.

In still other embodiments, bispecific antibody-directed delivery of therapeutics or prodrug polymers to in vivo targets can be combined with bispecific antibody delivery of radionuclides, such that combination chemotherapy and radioimmunotherapy is achieved. Each therapy can be conjugated to the targetable conjugate and administered simultaneously, or the nuclide can be given as part of a first targetable conjugate and the drug given in a later step as part of a second targetable conjugate.

In another embodiment, cytotoxic agents may be conjugated to a polymeric carrier, and the polymeric carrier may subsequently be conjugated to the multivalent target binding protein. For this method, see Ryser et al., *Proc. Natl. Acad. Sci. USA*, 75:3867-3870 (1978), U.S. Pat. No. 4,699,784 and U.S. Pat. No. 4,046,722, which are incorporated herein by reference. Conjugation preferably does not significantly affect the binding specificity or affinity of the multivalent binding protein.

7. Use of Subhuman Primatized, Humanized, Chimeric and Human Antibodies for Treatment and Diagnosis Subhuman primatized, humanized, chimeric and human monoclonal antibodies, i.e., anti-CD20 MAbs and other MAbs described herein, in accordance with this invention are suitable for use in therapeutic methods and diagnostic methods. Accordingly, the present invention contemplates the administration of the subhuman primatized, humanized, chimeric and human antibodies of the present invention alone as a naked antibody or administered as a multimodal therapy, temporally according to a dosing regimen, but not conjugated to, a therapeutic agent. The efficacy of the naked anti-CD20 MAbs can be enhanced by supplementing naked antibodies with one or more other naked antibodies, i.e., MAbs to specific antigens, such as CD4, CD5, CD8, CD14, CD15, CD19, CD21, CD22, CD23, CD25, CD33, CD37, CD38, CD40, CD40L, CD46, CD52, CD54, CD74, CD80, CD126, B7, Ia, HM1.24, tenascin, MUC1, or HLA-DR, as well as with anti-angiogenesis antibodies (e.g., VEGF and P1GF antibodies) with one or more immunoconjugates of anti-CD20, or antibodies to theses recited antigens, conjugated with therapeutic agents, including drugs, toxins, immunomodulators, hormones, therapeutic radionuclides, etc., with one or more therapeutic agents, including drugs, toxins, immunomodulators, hormones, therapeutic radionuclides, etc., administered concurrently or sequentially or according to a prescribed dosing regimen, with the MAbs. Preferred B-cell antigens include those equivalent to human CD19, CD20, CD21, CD22, CD23, CD46, CD52, CD74, CD80, and CD5 antigens. Preferred T-cell antigens include those equivalent to human CD4, CD8 and CD25 (the IL-2 receptor) antigens. An equivalent to HLA-DR antigen can be used in treatment of both B-cell and T-cell disorders. Particularly preferred B-cell antigens are those equivalent to human CD19, CD22, CD21, CD23, CD74, CD80, and HLA-DR antigens. Particularly preferred T-cell antigens are those equivalent to human CD4, CD8 and CD25 antigens. CD46 is an antigen on the surface of cancer cells that block complement-dependent lysis (CDC).

Further, the present invention contemplates the administration of an immunoconjugate for therapeutic uses in B cell lymphomas and other disease or disorders. An immunoconjugate, as described herein, is a molecule comprising an antibody component and a therapeutic agent, including a peptide which may bear the or therapeutic agent. An immunoconjugate retains the immunoreactivity of the antibody component, i.e., the antibody moiety has about the same or slightly reduced ability to bind the cognate antigen after conjugation as before conjugation.

Also, the present invention contemplates the administration of an immunoconjugate for therapeutic uses in myeloid leukemias, in which CD33, CD45, CD66, and other granulocyte-associated antigens are targeted.

A wide variety of therapeutic reagents can be advantageously conjugated to the antibodies of the invention. The therapeutic agents recited here are those agents that also are usefulfor administration separately with the naked antibody as described above. Therapeutic agents include, for example, chemotherapeutic drugs such as vinca alkaloids, anthracyclines, epidophyllotoxins, taxanes, antimetabolites, alkylating agents, antibiotics, Cox-2 inhibitors, antimitotics, antiangiogenic and apoptotoic agents, particularly doxorubicin, methotrexate, taxol, CPT-11, camptothecans, and others from these and other classes of anticancer agents, and the like. Other useful cancer chemotherapeutic drugs for the preparation of immunoconjugates and antibody fusion proteins include nitrogen mustards, alkyl sulfonates, nitrosoureas, triazenes, folic acid analogs, COX-2 inhibitors, pyrimidine analogs, purine analogs, platinum coordination complexes, including oxaliplatin, hormones, and the like. Suitable chemotherapeutic agents are described in REMINGTON'S PHARMACEUTICAL SCIENCES, 19th Ed. (Mack Publishing Co., 1995), and in GOODMAN AND GILMAN'S THE PHARMACOLOGICAL BASIS OF THERAPEUTICS, 7th Ed. (MacMillan Publishing Co., 1985), as well as revised editions of these publications. Other suitable chemotherapeutic agents, such as experimental drugs, are known to those of skill in the art.

Additionally, a chelator such as DTPA, DOTA, TETA, or NOTA or a suitable peptide, to which a detectable label, such as a fluorescent molecule, or cytotoxic agent, such as a heavy metal or radionuclide, can be conjugated. For example, a therapeutically useful immunoconjugate can be obtained by conjugating a photoactive agent or dye to an antibody composite. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), PHOTODYNAMIC THERAPY OF TUMORS AND OTHER DISEASES (Libreria Progetto 1985); van den Bergh, *Chem. Britain* 22:430 (1986)). Moreover, monoclonal antibodies have been coupled with photo-activated dyes for achieving phototherapy. Mew et al., *J. Immunol.* 130:1473 (1983); idem., *Cancer Res.* 45:4380 (1985); Oseroff et al., *Proc. Natl. Acad. Sci. USA* 83:8744 (1986); idem., *Photochem. Photobiol.* 46:83 (1987); Hasan et al., *Prog. Clin. Biol. Res.* 288:471 (1989); Tatsuta et al., *Lasers Surg. Med.* 9:422 (1989); Pelegrin et al., *Cancer* 67:2529 (1991). However, these earlier studies did not include use of endoscopic therapy applications, especially with the use of antibody fragments or subfragments. Thus, the present invention contemplates the therapeutic use of immunoconjugates comprising photoactive agents or dyes.

A toxin, such as *Pseudomonas* exotoxin, may also be complexed to or form the therapeutic agent portion of an antibody fusion protein of an anti-CD20 antibody of the present invention. Other toxins suitably employed in the preparation of such conjugates or other fusion proteins, include ricin, abrin, ribonuclease (RNase), DNase I, *Staphylococcal* enterotoxin-A, pokeweed antiviral protein, gelonin, diphtherin toxin, *Pseudomonas* exotoxin, and *Pseudomonas* endotoxin. See, for example, Pastan et al., *Cell* 47:641 (1986), and Goldenberg, *CA—A Cancer Journal for Clinicians* 44:43 (1994). Additional toxins suitable for use in the present invention are known to those of skill in the art and are disclosed in U.S. Pat. No. 6,077,499, which is incorporated in its entirety by reference.

An immunomodulator, such as a cytokine may also be conjugated to, or form the therapeutic agent portion of an antibody fusion protein or be administered with the humanized anti-CD20 or other lymphoma antibodies of the present invention. Suitable cytokines for the present invention include, but are not limited to, interferons and interleukins, as described below.

8. Preparation of Immunoconjugates

Any of the antibodies or antibody fusion proteins of the present invention can be conjugated with one or more therapeutic agent. Generally, one therapeutic agent is attached to each antibody or antibody fragment, but more than one therapeutic agent agent can be attached to the same antibody or antibody fragment. The antibody fusion proteins of the present invention comprise two or more antibodies or fragments thereof and each of the antibodies that composes this fusion protein can contain a therapeutic agent agent. Additionally, one or more of the antibodies of the antibody fusion protein can have more than one therapeutic agent attached. Further, the therapeutic agents do not need to be the same but can be different therapeutic agents. For example, one can attach a drug and a radioisotope to the same fusion protein. Particulary, an IgG can be radiolabeled with $^{131}$I and attached to a drug. The $^{131}$I can be incorporated into the tyrosine of the IgG and the drug attached to the epsilon amino group of the IgG lysines. The therapeutic agents also can be attached to reduced SH groups and to the carbohydrate side chains.

Bispecific antibodies of the present invention are useful in pretargeting methods and provide a preferred way to deliver two therapeutic agents to a subject. U.S. Ser. No. 09/382,186 discloses a method of pretargeting using a bispecific antibody, in which the bispecific antibody is labeled with $^{125}$I and delivered to a subject, followed by a divalent peptide labeled with $^{99m}$Tc. The delivery results in excellent tumor/normal tissue ratios for $^{125}$I and $^{99m}$Tc, thus showing the utility of two diagnostic radioisotopes. Any combination of known therapeutic agents agents can be used to label the antibodies and antibody fusion proteins. The binding specificity of the antibody component of the mAb conjugate, the efficacy of the therapeutic agent or diagnostic agent and the effector activity of the Fc portion of the antibody can be determined by standard testing of the conjugates.

A therapeutic agent can be attached at the hinge region of a reduced antibody component via disulfide bond formation. As an alternative, such peptides can be attached to the antibody component using a heterobifunctional cross-linker, such as N-succinyl 3-(2-pyridyldithio)proprionate (SPDP). Yu et al., *Int. J. Cancer* 56: 244 (1994). General techniques for such conjugation are well-known in the art. See, e.g., Wong, CHEMISTRY OF PROTEIN CONJUGATION AND CROSS-LINKING (CRC Press, 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc., 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press, 1995). Alternatively, the therapeutic agent can be conjugated via a carbohydrate moiety in the Fc region of the antibody. The carbohydrate group can be used to increase the loading of the same peptide that is bound to a thiol group, or the carbohydrate moiety can be used to bind a different peptide.

Methods for conjugating peptides to antibody components via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, all of which are incorporated in their entirety by reference. The general method involves reacting an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

The Fc region is absent if the antibody used as the antibody component of the immunoconjugate is an antibody fragment. However, it is possible to introduce a carbohydrate moiety into the light chain variable region of a full length antibody or antibody fragment. See, for example, Leung et al., *J. Immunol.* 154: 5919 (1995); Hansen et al., U.S. Pat. No. 5,443,953 (1995), Leung et al., U.S. Pat. No. 6,254,868, all of which are incoporated in their entirety by reference. The engineered carbohydrate moiety is used to attach the therapeutic or diagnostic agent.

9. Pharmaceutically Acceptable Vehicles

The subhuman primatized, humanized, chimeric or human radiolabeled antibody to be delivered to a subject can consist of the mAb alone, immunoconjugate, fusion protein, or can comprise one or more pharmaceutically suitable vehicles, one or more additional ingredients, or some combination of these.

The immunoconjugate antibody of the present invention can be formulated according to known methods to prepare pharmaceutically useful compositions, whereby the immunoconjugate or naked antibody is combined in a mixture with a pharmaceutically suitable vehicle. Sterile phosphate-buffered saline is one example of a pharmaceutically suitable vehicle. Other suitable vehicles are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REM- INGTON'S PHARMACEUTICAL SCIENCES, 18th Edition (Mack Publishing Company 1990), and revised editions thereof.

The immunoconjugate or naked antibody of the present invention can be formulated for parenteral application, such as intravenous administration via, for example, bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic conjugate or naked antibody. Control-release preparations can be prepared through the use of polymers to complex or adsorb the immunoconjugate or naked antibody. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of an immunoconjugate or antibody from such a matrix depends upon the molecular weight of the immunoconjugate or antibody, the amount of immunoconjugate, antibody within the matrix, and the size of dispersed particles. Saltzman et al., *Biophys. J* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate, antibody fusion proteins, or naked antibody may also be administered to a mammal subcutaneously or even by other parenteral routes. Moreover, the administration may be by continuous infusion or by single or multiple boluses. In general, the dosage of an administered immunoconjugate, fusion protein or naked antibody for humans will vary depending upon such factors as the patient's age, weight, height, sex, general medical condition and previous medical history. Typically, it is desirable to provide the recipient with a dosage of immunoconjugate, antibody fusion protein or naked antibody that is in the range of from about 1 mg/kg to 20 mg/kg as a single intravenous infusion, although a lower or higher dosage also may be administered as circumstances dictate. This dosage may be repeated as needed, for example, once per week for 4-10 weeks, preferably once per week for 8 weeks, and more preferably, once per week for 4 weeks. It may also be given less frequently, such as every other week for several months. The dosage may be given through various parenteral routes, with appropriate adjustment of the dose and schedule.

For purposes of therapy, the immunoconjugate, fusion protein, or naked antibody is administered to a mammal in a therapeutically effective amount. A suitable subject for the present invention is usually a human, although a non-human animal subject is also contemplated. An antibody preparation is said to be administered in a "therapeutically effective amount" if the amount administered is physiologically significant. An agent is physiologically significant if its presence results in a detectable change in the physiology of a recipient mammal. In particular, an antibody preparation of the present invention is physiologically significant if its presence invokes an antitumor response or mitigates the signs and symptoms of an autoimmune disease state. A physiologically significant effect could also be the evocation of a humoral and/or cellular immune response in the recipient mammal.

10. Methods of Treatment

The present invention contemplates the use antibodies of the present invention as the primary composition for treatment of diseases such as a B-cell related malignancy, a T-cell malignancy or another lymphoma type. In addition, it is also useful for treating autoimmune diseases. In particular, the compositions described herein are particularly useful for treatment of various autoimmune diseases as well as indolent forms of B-cell lymphomas, aggressive forms of B-cell lymphomas, chronic lymphatic leukemias, acute lymphatic leukemias, and Waldenström's macroglobulinemia, multiple myeloma. Also, T-cell diseases such as T-cell leukemia or mycosis fungoides can be treated. For example, the humanized anti-CD22 antibody components and immunoconjugates can be used to treat both indolent and aggressive forms of non-Hodgkin's lymphoma. An autoimmune disease is selected from the group consisting of acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis ubiterans, Sjogren's syndrome, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, and fibrosing alveolitis.

The compositions for treatment contain at least one humanized, chimeric or human monoclonal antibody alone or in combination with other antibodies, such as other humanized, chimeric, or human antibodies, therapeutic agents or immunomodulators. In particular, combination therapy with a fully human antibody is also contemplated and is produced by the methods as set forth above.

Conjugated antibodies to the same or different epitope or antigen may be also be combined with one or more of the antibodies of the present invention. For example, a humanized, chimeric or human conjugated anti-CD22 antibody may be combined with another subhuman primatized, humanized, chimeric or human conjugated anti-CD22, a subhuman primatized, humanized, chimeric or human conjugated anti-CD22 antibody may be combined with an anti-CD22 immunoconjugate. Alternatively, various such combinataions can be made with different lymphoma-associated antibodies, as described above. A fusion protein of a subhuman primatized, humanized, chimeric or human CD22 antibody and a toxin or immunomodulator, or a fusion protein of at least two different B-cell antibodies (e.g., a CD20 and a CD22 mAb) may also be used in this invention. Many different antibody combinations, targeting at least two different antigens associated with B-cell or other lymphoma or autoimmune disorders, as listed already above, may be constructed, either as partly conjugated with a therapeutic agent or immunomodulator, or merely in combination with another therapeutic agents, such as a cytotoxic drug or with radiation.

As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12 and IL-18), colony stimulating factors (e.g., granulocyte-colony stimulating factor (G-CSF) and granulocyte macrophage-colony stimulating factor (GM-CSF)), interferons (e.g., interferons-α, -β, and -γ), the stem cell growth factor designated "S1 factor," erythropoietin and thrombopoietin. Examples of suitable immunomodulator moieties include IL-2, IL-6, IL-10, IL-12, IL-18, interferon-γ, TNF-α, and the like. Alternatively, subjects can receive conjugated anti-CD20 antibodies and a separately administered cytokine, which can be administered before, concurrently or after administration of the naked or conjugated anti-CD20 antibodies. As discussed supra, the anti-CD22 antibody may also be conjugated to the immunomodulator. The immunomodulator may also be conjugated to a hybrid antibody or hybrid antibody fragments or subfragments (single-chain binding proteins, or sFv's) consisting of one or more antibodies or subfragments binding to different antigens.

Multimodal therapies of the present invention further include immunotherapy with conjugated anti-CD22 antibodies supplemented with administration of anti-CD20, anti-CD19, anti-CD21, anti-CD74, anti-CD80, anti-CD23, anti-CD46 or HLA-DR (including the invariant chain) antibodies in the form of fusion proteins or as immunoconjugates. These antibodies include polyclonal, monoclonal, primatized subhuman, chimeric, human or humanized antibodies that recognize at least one epitope on these antigenic determinants. Anti-CD19 and anti-CD22 antibodies are known to those of skill in the art. See, for example, Ghetie et al., *Cancer Res.* 48:2610 (1988); Hekman et al., *Cancer Immunol. Immunother.* 32:364 (1991); Longo, *Curr. Opin. Oncol.* 8:353 (1996) and U.S. Pat. Nos. 5,798,554 and 6,187,287, incorporated in their entirety by reference.

In another form of multimodal therapy, subjects receive conjugated antibodies, and/or immunoconjugates, in conjunction with standard cancer chemotherapy. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., *Eur. J. Haematol.* 51: 18 (1993). Other suitable combination chemotherapeutic regimens are wellknown to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second-generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate and brostatin-1. In a preferred multimodal therapy, both chemotherapeutic drugs and cytokines are co-administered with an antibody, immunoconjugate or fusion protein according to the present invention. The cytokines, chemotherapeutic drugs and antibody or immunoconjugate can be administered in any order, or together.

Radionuclides useful as therapeutic agents, which substantially decay by beta-particle emission include, include but are not limited to Ac-225, P-32, P-33, Sc-47, Fe-59, Cu-64, Cu-67, Se-75, As-77, Sr-89, Y-90, Mo-99, Rh-105, Pd-109, Ag-111, I-125, I-131, Pr-142, Pr-143, Pm-149, Sm-153, Tb-161, Ho-166, Er-169, Lu-177, Re-186, Re-188, Re-189, Ir-194, Au-198, Au-199, Pb-211, Pb-212, and Bi-213. Maximum decay energies of useful beta-particle-emitting nuclides are preferably 20-5,000 keV, more preferably 100-4,000 keV, and most preferably 500-2,500 keV.

Radionuclides useful as therapeutic agents, which substantially decay with Auger-emitting particles include, but are not limited to Co-58, Ga-67, Br-80m, Tc-99m, Rh-103m, Pt-109, In-111, Sb-119, I-125, Ho-161, Os-189m and Ir-192. Maximum decay energy of these radionuclides is preferably less than 1,000 keV, more preferably less than 100 keV, and most preferably less than 70 keV.

Radionuclides useful as therapeutic agents, which substantially decay with generation of alpha-particles include, but are not limited to Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-9,000 keV, more preferably 3,000-8,000 keV, and most preferably 4,000-7,000 keV.

Radionuclides useful in therapies based on neutron capture procedures include, but are not limited to B-10, Gd-157 and U-235.

The embodiments of the invention may be further illustrated through examples which show aspects of the invention in detail. These examples illustrate specific elements of the invention and are not to be construed as limiting the scope thereof.

EXAMPLES

Antibodies

Epratuzumab is a humanized LL2 antibody and developed by Immunomedics Inc., Morris Plains, N.J. The humanization process replaces ~95% of the murine Ig sequence with the human IgG$_1$ sequence. Epratuzumab is internalized once it binds to the B epitope of the CD22 antigen (Stein, R. et al., *Cancer Immunol. Immunother.* 37(5):293-8, 1993) that corresponds to the third Ig domain (Kehrl, J. H. *B6 CD22 Workshop Panel Report, in Leukocyte Typing V. White Cell Differentiation Antigens*, S. F. Schlossman (ed.), Oxford University Press, p. 523-5, 1995). In vitro internalization was observed after five minutes and re-expression of as much as 50% of the antigen was reported to occur after 5 hours (Shih, L. B. et al. *Int J Cancer* 56(4):538-45, 1994).

The humanized anti-CD20 antibody, hA20, has been developed by Immunomedics, Inc., Morris Plains, N.J. This Mab binds to CD20 and, in contrast to the chimeric anti-CD20 MAb, rituximab, it is a CDR-grafted MAb that has less murine protein than the chimeric form. The hA20 MAb has IgG1(kappa) constant regions and the same humanV framework regionas as epratuzumab, the CD22 humanized MAb. The genes of CDR-grafted VH and Vk chains of hA20 were inserted into the pdHL2 plasmid vector, a DHFR-based amplifiable expression system, and transfected into the Sp2/0 murine myeloma cell line to generate the hA20-producing clones. Molecular characterization demonstrated that hA20 is similar, in its CDRs, to rituximab, except for one amino acid difference in the VH region. However, differences in the VH and Vk framework regions of hA20, due to the inclusion of more human constructs, are present. This hA20 antibody appears to compete with the binding of rituximab for various lymphoma cells, and has a similar dissociation constant to rituximab, as well as similar effects in vitro and in vivo against human lymphoma cell lines expressing CD20.

Therapy of Non-Hodgkin's Lymphoma (NHL)

A 66-year-old man presents with stage IV diffuse-large cell NHL, having relapsed after 3 courses of chemotherapy given in the prior two years. He is given a dose of two injections of $^{90}$Y-DOTA-epratuzumab (as labelled in accordance with Govinden, ibid.), one week apart, having 7.5 mCi/m$^2$ of $^{90}$Y administered by intravenous infusion with a total dose of 30 mg antibody protein each time. Six weeks later, his cervical lymph nodes and his splenomegaly appear to have been reduced markedly, and the patient is symptomatically improved and returns to work full time. Since he does not have a complete remission, a continuous therapy is instituted involving a combination of epratuzumab (360 mg/m$^2$ and hA20 (250 mg/m$^2$), given every other week for a total of 4 infusions, and then the combined antibody therapy course is repeated 12 weeks later. Three months after completion of the second therapy course with the combination of naked CD22 and CD20 antibodies, the patient has no evidence of disease by radiological scans or bone marrow biopsy, and is thus considered to be a complete response. At the next evaluation, 3 months later, his is still in a complete remission of his disease.

Therapy of T-Cell Leukemia

A patient refractive to prior chemotherapy and with advanced T-cell leukemia is given an infusion of 50 mg anti-CD25 humanized Mab conjugated with 20 mCi $^{90}$Y-DOTA, followed one week later with an infusion of CD25 Mab (anti-TAC humanized antibody) at a dose of 200 mg/m$^2$. Four weeks later, his blood count and marrow biopsy indicate a partial remission of his disease.

Therapy of Refractive Rheumatoid Arthritis

A patient presenting with severe, advanced rheumatoid arthritis affecting many joints, but particularly his knees, and now refractive to chemotherapy, is treated with a single infusion of a mixture of CD4 and CD20 humanized Mabs, totalling 50 mg, labelled with $^{90}$Y at a dose of 10 mCi/m$^2$. Two weeks later, he is given a dose of naked humanized antibodies consisting of 100 mg CD4 and 250 mg CD20 antibodies, and this is repeated once again two weeks later. The patient feels relief of his arthritis, particularly in his knees, 4 weeks later, and is able to walk better and even climb stairs, with almost no joint inflammation noted by his physician. Three months later, this course of therapy involving one infusion of the radiolabelled mixture of antibodies, followed by two infusions of naked CD4 and CD20 antibodies, is repeated, and the patient re-evaluated 6 weeks later. The physician notes marked improvement, such that the patient evidences only minimal pain and considerably better mobility of his extremities.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following embodiments.

All of the publications and patent applications and patents cited in this specification are herein incorporated in their entirety by reference.

We claimed:

1. A method for treating a B-cell-related malignancy disease in a human comprising administering to said human either
   (i) a conjugated anti-CD74 antibody or an antigen-binding fragment thereof
   and
   an unconjugated anti-CD20 antibody or an antigen-binding fragment thereof,
   wherein said conjugated anti-CD74 antibody or antigen-binding fragment thereof and said unconjugated anti-CD20 antibody or antigen-binding fragment thereof are administered concurrently or sequentially
   or
   (ii) a conjugated anti-CD20 antibody or an antigen-binding fragment thereof
   and
   an unconjugated anti-CD74 antibody, or an antigen-binding fragment thereof,
   wherein said conjugated anti-CD20 antibody or antigen-binding fragment thereof and said unconjugated anti-CD74 antibody or antigen-binding fragment thereof are administered concurrently or sequentially,
   wherein predosing with a non-radiolabeled antibody is not performed and wherein the unconjugated anti-CD20 or unconjugated anti-CD74 is added as a maintenance therapy to keep proliferating tumor cells from target escape.

2. The method of claim 1, wherein the conjugated anti-CD20 antibody or antigen-binding fragment thereof is a humanized A20 (hA20) antibody or antigen-binding fragment thereof.

3. The method of claim 1, wherein
   in (i), said unconjugated anti-CD20 antibody or antigen-binding fragment thereof is administered simultaneously with said conjugated anti-CD74 antibody or antigen-binding fragment thereof, and
   in (ii), said unconjugated anti-CD74 antibody or antigen-binding fragment thereof is administered simultaneously with said conjugated anti-CD20 antibody or antigen-binding fragment thereof.

4. A method for treating a B-cell related malignancy disease in a human comprising administering to said human a bispecific antibody that binds to both CD74 and CD20, said bispecific antibody comprising either:
   (i) a conjugated anti-CD74 antibody or antigen-binding fragment thereof and an unconjugated anti-CD20 antibody or antigen binding fragment thereof, or
   (ii) a conjugated anti-CD20 antibody or antigen-binding fragment thereof and an unconjugated anti-CD74 antibody or antigen-binding fragment thereof,
   wherein the unconjugated anti-CD20 or anti-CD74 is a maintenance therapy to keep proliferating tumor cells from target escape.

5. The method of claim 1, wherein, in either (i) or (ii), said unconjugated antibody or antigen-binding fragment thereof is administered after said conjugated antibody or antigen-binding fragment thereof.

6. The method of claim 1, wherein said conjugated and unconjugated antibody or antigen-binding fragment thereof is a human or humanized antibody or antigen-binding fragment thereof.

7. The method of claim 1, wherein said conjugated antibody or antigen-binding fragment thereof is conjugated to a therapeutic agent selected from the group consisting of a drug, a toxin, an immunomodulator, a chelator, a boron compound, a photoactive agent, and a radionuclide.

8. The method of claim 1, wherein the B-cell-related malignancy disease is a B-cell lymphoma, B-cell acute lymphocytic leukemia, B-cell chronic lymphocytic leukemia, or multiple myeloma.

9. The method of claim 1, wherein said conjugated antigen-binding fragment thereof is conjugated to 90Y-DOTA.

10. The method of claim 1, wherein the B-cell-related malignancy disease is non-Hodgkin's lymphoma (NHL).

11. The method of claim 1, wherein the antigen-binding fragment is selected from the group consisting of F(ab)$_2$, Fab, Fv, sFv, scFv and diabody.

12. The method of claim 7, wherein said conjugated antibody or antigen-binding fragment thereof is conjugated to a drug selected from the group consisting of an antimitotic agent, an alkylating agent, an antimetabolite agent, an antiangiogenic agent, an apoptotic agent, an alkaloid agent, and antibiotic and a combination thereof.

13. The method of claim 7, wherein said conjugated antibody or antigen-binding fragment thereof is conjugated to a drug selected from the group consisting of a nitrogen mustard, an ethylenimine, an alkyl sulfonate, a nitrosourea, a triazene, a folic acid analog, an anthracycline, a taxane, a COX-2 inhibitor, a pyrimidine analog, a purine analog, an antibiotic, an enzyme, an epipodophyllotoxin, a platinum coordination complex, a vinca alkaloid, a substituted urea, a methyl hydrazine derivative, an adrenocortical suppressant, an endostatin, a taxol, a camptothecin, a doxorubicin, and a combination thereof.

14. The method of claim 7, wherein said conjugated antibody or antigen-binding fragment thereof is conjugated to a drug selected from the group consisting of cyclophosphamide, etoposide, vincristine, procarbazine, prednisone, carmustine, doxorubicin, methotrexate, bleomycin, dexamethasone, phenyl butyrate, bryostatin-1, and leucovorin.

15. The method of claim 7, wherein said conjugated antibody or antigen-binding fragment thereof is conjugated to a toxin selected from the group consisting of ricin, abrin, alpha toxin, saporin, ribonuclease (RNase), DNase I, *Staphylococcal* enterotoxin-A, pokeweed antiviral protein, gelonin, diphtherin toxin, *Pseudomonas* exotoxin, and *Pseudomonas* endotoxin.

16. The method of claim 7, wherein said conjugated antibody or antigen-binding fragment thereof is conjugated to an immunomodulator selected from the group consisting of a cytokine, a stem cell growth factor, a lymphotoxin, a hematopoietic growth factor, a colony stimulating factor (CSF), an interferon (IFN), erythropoietin, thrombopoietin and a combination thereof.

17. The method of claim 7, wherein said conjugated antibody or antigen-binding fragment thereof is conjugated to an immunomodulator selected from the group consisting of IL-I, IL-2, IL-3, IL-6, IL-10, IL-12, IL-18, G-CSF, GM-CSF, interferon-α, -β or γ, TNF-α and stem cell growth factor.

18. The method of claim 7, wherein said radionuclide is bound to said chelator selected from the group consisting of DTPA, DOTA, TETA and NOTA.

19. The method of claim 7, wherein said therapeutic agent is selected from the group consisting of tumor necrosis factor, hematopoietic growth factor, colony stimulating factor, interferon, and stem cell growth factor.

20. The method of claim 18, wherein said radionuclide decays by beta particle emission and is selected from the group consisting of P-32, P-33, Sc-47, Fe-59, Cu-64, Cu-67, Se-75, As-77, Sr-89, Y-90, Mo-9, Rh-105, Pd-109, Ag-111, I-125, I-131, Pr-142, Pr-143, Pm-149, Sm-153, Tb-161, Ho-166, Er-169, Lu-177, Re-186, Re-188, Re-189, Ir-194, Au-198, Au-199, Pb-211, Pb-212, and Bi-213.

21. The method of claim 20, wherein said radionuclide has a maximum decay energy of 20-5,000 keV.

22. The method of claim 20, wherein said radionuclide has a maximum decay energy of 100-4,000 keV.

23. The method of claim 20, wherein said radionuclide has a maximum decay energy of 500-2,500 keV.

24. The method of claim 18, wherein said radionuclide decays by Auger particle emission and is selected from the group consisting of Co-58, Ga-67, Br-80rn, Tc-99m, Rh-103m, Pt-109, In-111, Sb-119, I-125, Ho-161, Os-189m and Ir-192.

25. The method of claim 24, wherein said radionuclide has a maximum decay energy of less than 1,000 keV.

26. The method of claim 24, wherein said radionuclide has a maximum decay energy of less than 100 keV.

27. The method of claim 24, wherein said radionuclide has a maximum decay energy of less than 70 keV.

28. The method of claim 18, wherein said radionuclide decays by alpha-particle emission and is selected from the group consisting of Ac-225, Dy-152, At-211, Bi-212, Ra-223, Rn-219, Po-215, Bi-211, Fr-221, At-217, Bi-213 and Fm-255.

29. The method of claim 28, wherein said radionuclide has a maximum decay energy of 2,000-9,000 keV.

30. The method of claim 28, wherein said radionuclide has a maximum decay energy of 3,000-8,000 keV.

31. The method of claim 28, wherein said radionuclide has a maximum decay energy of 4,000-7,000 keV.

32. The method of claim 7, wherein said therapeutic agent is used in photodynamic therapy or neutron capture procedures.

33. The method of claim 32, wherein said photodynamic therapy uses metal complexes, and said metal complexes are selected from the group consisting of zinc, aluminum, gallium, lutetium and palladium.

34. The method of claim 32, wherein said neutron capture procedures uses a radionuclide selected from the group consisting of B-10, Gd-157 and U-235.

35. The method of claim 8, wherein said B-cell lymphoma is an indolent form of B-cell lymphoma or an aggressive form of B-cell lymphoma.

36. The method of claim 1, wherein a ratio of targeted anti-CD20 or anti-CD74 antigen on diseased tissue exceeds that on normal tissue by a ratio of more than 1.6:1.

37. The method of claim 1, wherein a ratio of targeted anti-CD20 or anti-CD74 antigen on diseased tissue exceeds that on normal tissue by a ratio of 5:1.

38. A method for treating a B-cell related malignancy disease comprising administering to a human a therapeutic composition comprising:
(a) a pharmaceutically acceptable vehicle containing unconjugated anti-CD20 antibody, or an antigen-binding fragment thereof, or unconjugated single chain antibody fusion protein, said antibody fusion protein comprising a recombinantly produced antigen-binding molecule in which two or more of the same or different single-chain antibodies, or two or more of the same or different antigen-binding fragments are linked,
wherein said unconjugated antibody or antigen-binding fragment thereof or said unconjugated fusion protein targets CD20, and said fusion protein or antigen-binding fragment comprises the variable domains, or the CDRs of the heavy and light chains of said CD20 antibody; and
(b) a pharmaceutically acceptable vehicle containing a conjugated humanized monoclonal antibody or antigen-binding fragment thereof that binds CD74, said antibody or antigen-binding fragment thereof being conjugated to doxorubicin
wherein (a) and (b) are administered concurrently or sequentially.

39. The method of claim 38, wherein the B-cell related malignancy disease is a leukemia.

40. The method of claim 1, wherein said B-cell-related malignancy disease is multiple myeloma.

41. A method for treating a B-cell-related malignancy disease in a human as claimed in claim 1, comprising administering to said human either (a) a combination consisting of (i) a conjugated anti-CD74 antibody or antigen-binding fragment thereof and (ii) an unconjugated anti-CD20 antibody or antigen-binding fragment thereof, and (iii) at least one member selected from the group consisting of a pharmaceutically acceptable vehicle, an immunomodulator, and a chemotherapeutic drug wherein said conjugated anti-CD74 antibody or antigen-binding fragment thereof and said unconjugated anti-CD20 antibody or antigen-binding fragment thereof are administered concurrently or sequentially;

or (b) a combination consisting of (i) a conjugated anti-CD20 antibody or antigen-binding fragment thereof and (ii) an unconjugated anti-CD74 antibody or antigen-binding fragment thereof, and (iii) at least one member selected from the group consisting of a pharmaceutically acceptable vehicle, an immunomodulator, and a chemotherapeutic drug wherein said conjugated anti-CD20 antibody or antigen-binding fragment thereof and said unconjugated anti-CD74 antibody or antigen-binding fragment thereof are administered concurrently or sequentially, and wherein predosing with a non-radiolabeled antibody is not performed and wherein the unconjugated anti-CD20 or unconjugated anti-CD74 is added as a maintenance therapy to keep proliferating tumor cells from target escape.

42. The method of claim 38, wherein the B-cell-related malignancy disease is a B-cell lymphoma, B-cell acute lymphocytic leukemia, B-cell chronic lymphocytic leukemia, or multiple myeloma.

43. The method of claim 38, wherein the B-cell-related malignancy disease is non-Hodgkin's lymphoma (NHL).

44. The method of claim 38, wherein the B-cell-related malignancy disease is multiple myeloma.

* * * * *